(12) United States Patent
Chen et al.

(10) Patent No.: US 9,696,318 B2
(45) Date of Patent: Jul. 4, 2017

(54) HYDROPHILIC FILM, PREPARATION METHOD AND APPLICATIONS THEREOF

(71) Applicant: 3M INNOVATIVE PROPERTIES COMPANY, St. Paul, MN (US)

(72) Inventors: Te-Wei Chen, Taiwan (CN); Huang Chin Hung, Taiwan (CN); Naiyong Jing, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/430,145

(22) PCT Filed: Sep. 12, 2013

(86) PCT No.: PCT/US2013/059395
§ 371 (c)(1),
(2) Date: Mar. 20, 2015

(87) PCT Pub. No.: WO2014/046955
PCT Pub. Date: Mar. 27, 2014

(65) Prior Publication Data
US 2015/0241441 A1 Aug. 27, 2015

(30) Foreign Application Priority Data
Sep. 24, 2012 (CN) .......................... 2012 1 0362882

(51) Int. Cl.
*G01N 33/66* (2006.01)
*C08J 7/04* (2006.01)
(Continued)

(52) U.S. Cl.
CPC ............... *G01N 33/66* (2013.01); *C08J 7/06* (2013.01); *C23C 18/1266* (2013.01); *Y10T 428/24421* (2015.01); *Y10T 436/144444* (2015.01)

(58) Field of Classification Search
CPC ...................................................... G01N 33/66
See application file for complete search history.

(56) References Cited

U.S. PATENT DOCUMENTS 4,824,640 A  4/1989  Hildenbrand
5,262,475 A  11/1993  Creasy
(Continued)

FOREIGN PATENT DOCUMENTS

CN  101579672 A  11/2009
EP  1385002  1/2004
(Continued)

OTHER PUBLICATIONS

International Search Report for PCT International Application No. PCT/US2013/059395, mailed on Mar. 11, 2014, 3 pages.

*Primary Examiner* — Paul Hyun
(74) *Attorney, Agent, or Firm* — Qiang Han (57) ABSTRACT

The present invention provides a hydrophilic film that causes a liquid to diffuse rapidly in a single direction. The hydrophilic film comprises a substrate having a texture of parallel sunken and raised patterns, and a hydrophilic coat comprising a coat of silicon dioxide particles. The present invention also provides a method for preparing the hydrophilic film. The method comprises: preparing an aqueous dispersion of silicon dioxide particles, wherein the average size of the silicon dioxide particles is 1 to 60 nm, and the concentration of the silicon dioxide particles is 0.05% to 15% by weight; coating the aqueous dispersion of silicon dioxide particles on a substrate, wherein the substrate has a texture of parallel sunken and raised patterns; and drying the substrate coated with the aqueous dispersion of silicon dioxide particles.

19 Claims, 9 Drawing Sheets

(51) Int. Cl.
    *C23C 18/00*     (2006.01)
    *B01L 99/00*     (2010.01)
    *C23C 18/12*     (2006.01)
    *C08J 7/06*     (2006.01)

(56) References Cited

U.S. PATENT DOCUMENTS

| | | | |
|---|---|---|---|
| 5,322,063 A | 6/1994 | Allen | |
| 7,378,451 B2 | 5/2008 | Levitt | |
| 8,377,390 B1* | 2/2013 | Brueck | B01J 19/0093 |
| | | | 264/293 |
| 2004/0067166 A1* | 4/2004 | Karinka | B01L 3/502723 |
| | | | 422/82.03 |
| 2007/0266777 A1* | 11/2007 | Bergman | B01J 20/28014 |
| | | | 73/61.41 |
| 2008/0056947 A1* | 3/2008 | Glauser | A61B 5/1411 |
| | | | 422/68.1 |
| 2011/0052475 A1* | 3/2011 | Barati | C01B 33/023 |
| | | | 423/350 |
| 2014/0017123 A1* | 1/2014 | Babic | A61B 5/1411 |
| | | | 422/68.1 |

FOREIGN PATENT DOCUMENTS

| | | |
|---|---|---|
| EP | 1760120 | 3/2009 |
| WO | WO 97-30344 | 8/1997 |
| WO | WO 2009/140482 | 11/2009 |

\* cited by examiner

HYDROPHILIC FILM, PREPARATION METHOD AND APPLICATIONS THEREOF

CROSS REFERENCE TO RELATED APPLICATION

This application claims the benefit of Chinese Patent Application No. 201210362882.7, filed Sep. 24, 2012, the disclosure of which is incorporated by reference herein in its entirety.

FIELD OF THE INVENTION

The present invention relates to a hydrophilic film, particularly to a hydrophilic film that causes a liquid to diffuse in a certain direction. The present invention also relates to a method for preparing the hydrophilic film, and to applications of the hydrophilic film.

BACKGROUND OF THE INVENTION

Hydrophilic films have applications in a variety of fields. One of the methods to make hydrophilic films is to modify the substrate film with a hydrophilic coat layer. It was reported in prior art that a coat of nanometer silicon dioxide was applied on the substrate to improve hydrophilicity, and thereby to improve liquid flow rate and antifogging property. However, with regard to the hydrophilic films of the prior art, direction of liquid diffusion on a hydrophilic surface cannot be controlled; therefore, diffusion rates of the liquid in different directions are the same.

For applications in some fields, it is necessary for liquid to diffuse in a certain direction. For example, in modern medical diagnoses, it is necessary to use various types of analytical test strips. These test strips are used to test levels of glucose, cholesterol, protein and other substances in blood and urine. In order to monitor blood sugar level of a diabetic patient, it is necessary to use a blood glucose meter and test strips to conduct several tests every day. Since liquid flow on current test strips is not directional, a considerable amount of blood samples collected in the tests is not utilized. In order to increase utilization rate of the blood sample and to reduce the amount of blood used in each test, it is desired to make the blood sample flow rapidly in a certain direction on the test strips.

Thus, there is a need to develop a hydrophilic film that can cause liquid to diffuse rapidly in a certain direction.

SUMMARY OF THE INVENTION

The objective of the present invention is to provide a hydrophilic film and a method for preparing the same.

According to one aspect of the present invention, there is provided a hydrophilic film that causes a liquid to diffuse rapidly in a single direction. The hydrophilic film comprises a substrate having a texture of parallel sunken and raised patterns, and a hydrophilic coat comprising a coat of silicon dioxide particles.

According to another aspect of the present invention, there is provided a method for preparing the hydrophilic film, the method comprising: preparing an aqueous dispersion of silicon dioxide particles, wherein the average size of the silicon dioxide particles is 1 to 60 nm, and the concentration of the silicon dioxide particles is 0.05% to 15% by weight; coating the aqueous dispersion of silicon dioxide particles on a substrate, wherein the substrate has a texture of parallel sunken and raised patterns; and drying the substrate coated with the aqueous dispersion of silicon dioxide particles.

DESCRIPTION OF THE DRAWINGS

FIG. 1 (A) is a schematic cross section drawing of a flat PET film of a prior art, and a comparison of liquid diffusion effects before and after hydrophilic treatment. FIG. 1 (B) is a schematic cross section drawing of a hydrophilic film according to an Example of the present invention, and a comparison of liquid diffusion effects before and after hydrophilic treatment.

FIGS. 2 (A)-(C) show liquid diffusion test results of a Comparative Example and two Examples of the present invention, respectively.

FIGS. 5 (A)-(G) show binding strength test results of hydrophilic film examples of the present invention.

DETAILED DESCRIPTION OF THE INVENTION

According to one aspect of the present invention, there is provided a hydrophilic film that causes a liquid to diffuse rapidly in a single direction. The hydrophilic film comprises a substrate having a texture of parallel sunken and raised patterns, and a hydrophilic coat comprising a coat of silicon dioxide particles.

There is no particular restriction on substrate materials, which include thermoplastic materials, and such substrate materials can be selected from a group consisting of polyester, polyether, polyamide, polyolefin, polyacrylic acid and glass. Particular examples include polyethylene terephthalate (PET), polyvinyl chloride (PVC) or polyacrylic acid (PAA).

The substrate of the present invention may be a single-layer or a double-layer structure comprised of the above-described materials. A substrate having a single-layer structure as described herein refers to a substrate made from a single material, while a substrate having a double-layer structure refers to a substrate made from one base material with another material being formed on the base material.

Figure 1:
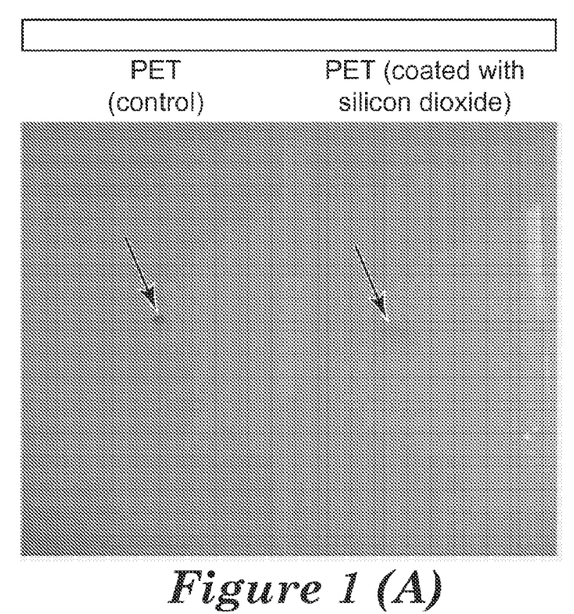
Figure 2:
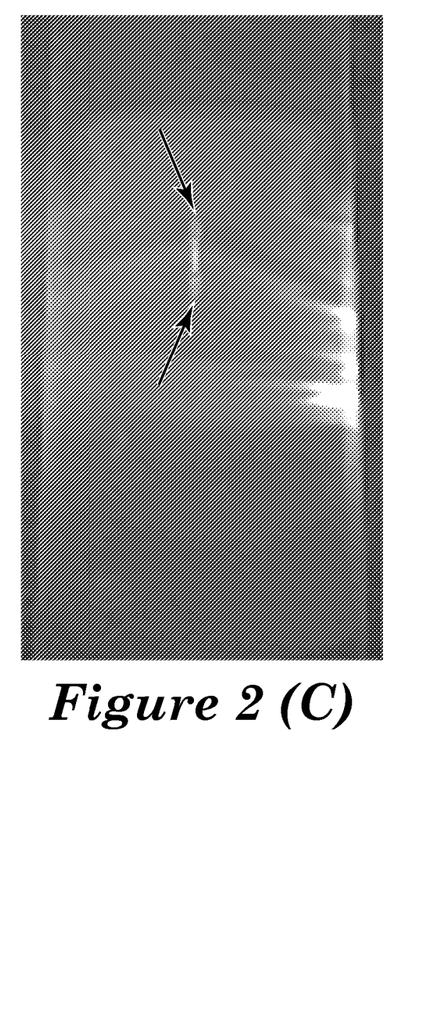

For example, an example of the substrate that can be used for the present invention is 3M™ Brightness Enhancement Film (BEF). The BEF may be a double-layer structure, that is, a substrate of PET material as a base material coated with a PAA material on its surface, and embossed with micro-replication technique and then solidified to form a PAA micro-replicated prism structure and to provide a texture of regular parallel sunken and raised patterns using the micro-replicated prism structure. In one example, the texture of sunken and raised patterns of the BEF substrate has such a dimension that the distance D1 between the peaks of two adjacent prisms is about 50 μm, while the distance D2 between the peak and the bottom of the prism is about 25 μm (as shown in FIG. 1 (B)). However, it should be understood that there are virtually no restrictions on the dimension and shape of the texture of sunken and raised patterns of the substrate according to the present invention. For example, in other examples, other texture of sunken and raised patterns of the substrate with a dimension in the order of microns may be selected as the substrate, for example, a micro-replicated prism structure with a distance between two adjacent highest points or lowest points in the texture of parallel sunken and raised patterns being in a range from 1 μm to 500 μm, or from 2 μm to 300 μm, or from 5 μm to 150 μm, while the vertical distance between the adjacent highest and lowest points in the texture of parallel sunken and raised patterns being in a range from 0.5 μm to 250 μm, or from 1 μm to 150 μm, or from 2.5 μm to 75 μm, or various forms of BEF substrate with the distance D1 between the two adjacent highest points or lowest points in the texture of parallel sunken and raised patterns being 62 μm, 50 μm, 24 μm or 17 μm, while the depth D2 being 31 μm, 25 μm, 12 μm or 8.5 μm. Thus, it can be seen that there is no particular restriction on the dimension of the texture of sunken and raised patterns of the substrate, while the depth of the texture of parallel sunken and raised patterns can be about half of the distance between the two adjacent highest points or lowest points in the texture of parallel sunken and raised patterns, but is not limited thereto. In addition, the texture of sunken and raised patterns of the substrate may also be a texture of square or round patterns, etc. Of course, the substrate materials are not limited to BEF. For example, the substrate can be made from glass as a base material and a thermoplastic material on the glass to form the texture of sunken and raised patterns, or it can be made from two thermoplastic materials coupled with each other. The substrate is not limited to a two-layer structure. In other words, the substrate can be a single-layer structure, i.e., a texture of sunken and raised patterns made from a single material, for example, by micro-replication technique or by milling and cutting processing.

In order to impart hydrophilicity to the substrate, surface modification is needed. The hydrophilic surface modification can be achieved by coating a layer of silicon dioxide on the substrate. In order to maintain the texture of regular unidirectional sunken and raised patterns while imparting hydrophilicity to the substrate, it is necessary to prevent the texture of sunken and raised patterns on the substrate surface from being covered up due to excessively large particle size of silicon dioxide and an excessively thick coated layer. Therefore, it is imperative to select silicon dioxide particles having an appropriate range of particle sizes, and to control concentration of the silicon dioxide solution used in the coating process, so that a silicon dioxide layer with an appropriate thickness is evenly coated on the texture of sunken and raised patterns on the substrate surface. The substrate becomes hydrophilic after being coated with a layer of silicon dioxide nanoparticles, and has a larger surface area than a substrate with a flat surface. Moreover, when a liquid is applied on a substrate coated with a layer of silicon dioxide nanoparticles, the liquid flows preferentially in one direction along the sunken microtexture.

The hydrophilic coat can be formed by coating an aqueous dispersion of silicon dioxide particles. Since hydrophilicity is in direct proportion to the amount of hydroxyl groups on the surface of silicon dioxide particles, silicon dioxide particles with a smaller average size have a larger surface area and more hydroxyl groups than silicon dioxide particles with a larger average size, when compared based on the same volume or weight. Therefore, the smaller the average size of silicon dioxide particles, the better the hydrophilic effect of the hydrophilic film formed by the silicon dioxide particles. Nowadays, silicon dioxide particles with an average size of smaller than 1 nm can be synthesized by sol-gel process technology in the laboratory. The average size of the silicon dioxide particles used for the hydrophilic coat of silicon dioxide particles of the present invention may be 1 to 60 nm, preferably 4 to 60 nm, and more preferably 4 to 25 nm. The hydrophilic coat of silicon dioxide particles is formed by coating an aqueous dispersion of silicon dioxide particles. In the process of preparing the hydrophilic film of the present invention, concentration of the aqueous dispersion of silicon dioxide nanoparticles may be 0.05%-15% by weight, preferably 0.5%-10% by weight, and more preferably 1%-10% by weight. In the present invention, for the aqueous dispersion of silicon dioxide particles for preparing the silicon dioxide coat, the silicon dioxide particles can be selected from the group consisting of the first group of silicon dioxide particles, the second group of silicon dioxide particles, the third group of silicon dioxide particles, and a combination thereof, wherein the average size of the first group of silicon dioxide particles is no larger than 6 nm, the average size of the second group of silicon dioxide particles is larger than the first group of silicon dioxide particles but no larger than 25 nm, and the average size of the third group of silicon dioxide particles is larger than the second group of silicon dioxide particles but no larger than 60 nm.

In the process of preparing the hydrophilic film of the present invention, when the concentration of the aqueous dispersion of silicon dioxide particles is no more than 0.5% by weight, the silicon dioxide particles in the aqueous dispersion of silicon dioxide particles can be selected from the group consisting of the first group of silicon dioxide particles, the second group of silicon dioxide particles, the third group of silicon dioxide particles, and a combination thereof; when the concentration of the aqueous dispersion of silicon dioxide nanoparticles is from 0.5% to 10% by weight, the silicon dioxide particles in the aqueous dispersion of silicon dioxide particles is preferably selected from the group consisting of the first group of silicon dioxide particles, the second group of silicon dioxide particles, and a combination thereof; and when the concentration of the aqueous dispersion of silicon dioxide nanoparticles is from 10% to 15% by weight, the silicon dioxide particles in the aqueous dispersion of silicon dioxide particles is preferably selected from the first group of silicon dioxide particles.

FIG. 1 shows a comparison of liquid diffusion effects between a hydrophilic film of a prior art (FIG. 1 (A)) and a hydrophilic film of the present invention (FIG. 1 (B)). In the prior art, a chemically treated flat PET film is used as the substrate, while 3M™ BEF is used as the substrate in the present invention.

It can be seen from the schematic cross section drawings on top of FIG. 1 that the substrate of the present invention has a texture of repeated miniature prisms. It can be seen from FIG. 1 (A) that with regard to the PET film of the prior art, a liquid drop is unable to wet the PET film prior to hydrophilic treatment, and therefore it is difficult for the liquid drop to diffuse, as shown on the left side of FIG. 1 (A). After the hydrophilic treatment, the liquid drop is able to diffuse easily, but its diffusion rates in different directions are the same, thus forming a round liquid drop with an expanded area, as shown on the right side of FIG. 1 (A). It can be seen from FIG. 1 (B) that with regard to the BEF substrate used in the present invention, a liquid drop is unable to wet the film prior to hydrophilic treatment, and therefore it is difficult for the liquid drop to diffuse, as shown on the left side of FIG. 1 (B), even though there is a texture of sunken and raised patterns. After the hydrophilic treatment, the liquid drop is able to diffuse easily, and the liquid drop diffuses preferentially in one direction since there is a texture of repeated miniature prisms, thus forming a significantly stretched liquid drop, as shown on the right side of FIG. 1 (B).

According to another aspect of the present invention, there is provided a method for preparing the hydrophilic film, the method comprising preparing an aqueous dispersion of silicon dioxide particles, wherein the average size of the silicon dioxide particles is 1 to 60 nm, and the concentration of the silicon dioxide particles is 0.05% to 15% by weight; coating the aqueous dispersion of silicon dioxide particles on a substrate, wherein the substrate has a texture of parallel sunken and raised patterns; and drying the substrate coated with the aqueous dispersion of silicon dioxide particles.

In the method for preparing the hydrophilic film of the present invention, in order to enhance hydrophilic effect, the pH value of the silicon dioxide coating solution may be further optionally controlled to 2-5, and preferably 2-3, so that the amount of hydroxyl groups (—OH) in the silicon dioxide coating solution can be increased by acidification, and hydrophilic effect can be enhanced accordingly. In order to increase wetability on the substrate during the coating process, a certain amount of resin may be optionally added as an adhesive to the coating solution of silicon dioxide nanoparticles. Examples of the resin include acrylic resins or polyurethane resins. There is no restriction on the amount of the resin so used as long as it can provide desired adhesive effect. It is usually less 20% by weight, e.g., 0.1-20% by weight, preferably 1-12%, and more preferably 1-6%% by weight.

The aqueous silicon dioxide coating solution may also optionally contain other components such as a surfactant to enhance coating effect of the aqueous silicon dioxide coating solution. In some embodiments, a cationic surfactant may be selected as the surfactant, such as sodium dodecylsulfonate (DS-10) or polyvinyl alcohol (PVA), and the like.

There is no restriction on the type of acid for adjusting the pH value. It may be an inorganic acid or an organic acid. Examples of the acid include, but are not limited to, hydrochloric acid, sulfuric acid, formic acid, acetic acid, and the like.

Various conventional coating methods used in the art may be used for coating the aqueous dispersion of silicon dioxide nanoparticles on the substrate. Such methods include, but are not limited to, impregnation, screen printing coating, blade coating or spray coating, and the like.

After the coating, conventional coating methods used in the art may be used to dry the coat. For example, the coated substrate may be left to stay at 85° C. for 15 minutes. However, there is no restriction on the drying methods. Any methods that do not damage the silicon dioxide solution coated on the substrate surface, for example, natural drying by air at ambient temperature and the like, may be used for the present invention.

EXAMPLES

The following examples are presented to further illustrate the present invention, but they are not limiting the scope of the present invention.

I. Raw materials used in these examples are summarized as follows:

A. Silicon dioxide nanoparticles

ST-XS (particle size: 4 to 6 nm), ST-50 (particle size: 20 to 25 nm) and ST-XL (particle size: 40 to 60 nm), purchased from Nissan Chemical Industries, Ltd., Japan.

B. Water-based resin: NeoCryl A-1127, purchased from DSM Company, USA; and TEGO Variplus DS 50, purchased from Evonik Degussa Taiwan Ltd., Taiwan.

C. Hydrochloric acid (HCl, 35%), purchased from Shimakyu's Pure Chemicals, Japan.

D. Substrate:

3M™ Brightness Enhancement Film II NH (BEF2-T-155 n), which is a brightness enhancement film with a PAA micro-replicated prism structure formed on a PET substrate.

A 4-mil PET film treated with PT069 (corona/chemically treated PET film), purchased from KJ Applied Materials Co., Ltd.

E. Protective adhesive tape

3M™ Scotch 1T01L, a polyester tape with an acrylic adhesive having a low-tack and ATS (adhesive to steel) of 10-30 gf/in.

F. Sodium hydroxide (NaOH, 45% solution of sodium hydroxide), purchased from Yee Fong Chemical & Industrial Co., Ltd. (Taiwan).

In the present invention, pH value is measured by a pH-meter (purchased from METTLER TOLEDO).

All concentrations used herein are by weight, unless otherwise specified.

II. Method for preparing the hydrophilic film

1. Preparation of the Coating Solution

The aqueous dispersion of silicon dioxide nanoparticles is prepared from silicon dioxide nanoparticles with various particle sizes and deionized water. The aqueous dispersion of silicon dioxide nanoparticles is acidified with HCl (35%) to pH value of 3.0-2.0. A resin in an amount of 1-20% by weight may be optionally added as an adhesive to the acidified dispersion of silicon dioxide nanoparticles.

2. Coating of the Hydrophilic Film

The dispersion as prepared according to the above section 1 is evenly coated on the substrate with a wire-wound rod. The wet coat is about 50.3 μm thick and allowed to dry in air at ambient temperature, and is further dried at 85° C. for 15 min.

Examples 1-17

TABLE 1

Composition of the coating solution

| Example No. | Silicon dioxide part No. | Silicon dioxide concentration (wt %) | pH of solution | Resin addition |
| --- | --- | --- | --- | --- |
| Example 1 | ST-50 | 0.05 | 2.5 ± 0.5 | No |
| Example 2 | ST-XL | 0.05 | 2.5 ± 0.5 | No |
| Example 3 | ST-50 | 0.1 | 2.5 ± 0.5 | No |
| Example 4 | ST-XL | 0.5 | 2.5 ± 0.5 | No |
| Example 5 | ST-XS | 1 | 2.5 ± 0.5 | No |
| Example 6 | ST-XS | 3 | 2.5 ± 0.5 | No |
| Example 7 | ST-XS | 5 | 2.5 ± 0.5 | No |
| Example 8 | ST-XS | 10 | 2.5 ± 0.5 | No |
| Example 9 | ST-XS | 15 | 2.5 ± 0.5 | No |
| Example 10 | ST-50 | 1 | 2.5 ± 0.5 | No |
| Example 11 | ST-50 | 3 | 2.5 ± 0.5 | No |
| Example 12 | ST-50 | 10 | 2.5 ± 0.5 | No |
| Example 13 | ST-50 | 15 | 2.5 ± 0.5 | No |
| Example 14 | ST-XL | 1 | 2.5 ± 0.5 | No |
| Example 15 | ST-XL | 3 | 2.5 ± 0.5 | No |
| Example 16 | ST-XL | 10 | 2.5 ± 0.5 | No |
| Example 17 | ST-XL | 15 | 2.5 ± 0.5 | No |

The 3M™ Brightness Enhancement Film II NH (BEF2-T-155 n) is used as a substrate and coated with the coating solution as indicated in Table 1.

Comparative Example 1

A PET film treated with PT069, surface of which has not been subjected to any kind of hydrophilic treatment.

Comparative Example 2

A PET film treated with PT069 is used as a substrate, which is a flat PET film coated with a 3% aqueous dispersion of ST-XS silicon dioxide particles (particle size: 4-6 nm) with a pH value of 2.5±0.5 and then dried. Thickness of the coat is about 50.3 μm when wet.

Comparative Example 3

3M™ Brightness Enhancement Film II NH (BEF2-T-155 n), surface of which has not been subjected to any kind of hydrophilic treatment.

III. Characterization method
 1. Test of Hydrophilicity
 1-1. Liquid Drop Diffusion Test With regard to the isotropic hydrophilic films of the Comparative Examples 1 and 2, the method of the liquid drop diffusion test is to measure a round area formed on the film by liquid diffusion or wetting. A substrate printed with several identical circles is placed on a flat surface, and a test film is placed on the substrate. Then, a 3-μL drop of a dye solution is dropped in each circle on the test film with a microsyringe while the film surface is allowed to be in contact with the solution, but not with the tip of the microsyringe. The liquid drops are allowed to dry in air for at least 10 minutes, and diameters of the drops are visually observed.

It can be seen from Comparative Example 1 on the left side of FIG. 1 (A) and Comparative Example 2 on the right side that, when the film having the hydrophilic coat Comparative Example 2 is compared with the film without the hydrophilic coat of Comparative Example 1, the diameter of the circular area formed by water drop diffusion is 0.2 cm on the film without the hydrophilic coat, while the diameter of the circular area formed by water drop diffusion is 0.7 cm on the film having the hydrophilic coat, which shows a significant increase in the liquid drop diameter. In other words, coating of the hydrophilic does help liquid diffusion.

1-2. Diffusion Distance Test

The method of the diffusion distance test is to measure the distance by which the test solution diffuses in one direction on the test film. The test is time-dependant. First of all, a test film is placed on a flat surface, and a ruler is placed on the test film in parallel with the diffusion direction. Then, a 3-μL drop of a dye solution is dropped on each test film with a microsyringe while the film surface is allowed to be in contact with the solution, but not with the tip of the microsyringe. The diffusion distance advanced in every 10 minutes is recorded and it is determined if the diffusion of the dye drop is directional.

Test results of the examples and Comparative Examples are shown in Table 2.

TABLE 2

Directional diffusion test results of the examples and Comparative Examples

| Group | Directional diffusion |
|---|---|
| Comparative Example 2 | No |
| Example 1 | Yes |
| Example 2 | Yes |
| Example 3 | Yes |
| Example 4 | Yes |

TABLE 2-continued

Directional diffusion test results of the examples and Comparative Examples

| Group | Directional diffusion |
|---|---|
| Example 5 | Yes |
| Example 6 | Yes |
| Example 7 | Yes |
| Example 8 | Yes |
| Example 9 | Yes |
| Example 10 | Yes |
| Example 11 | Yes |
| Example 12 | Yes |
| Example 13 | Yes |
| Example 14 | Yes |
| Example 15 | Yes |
| Example 16 | Yes |
| Example 17 | Yes |

Figure 3:
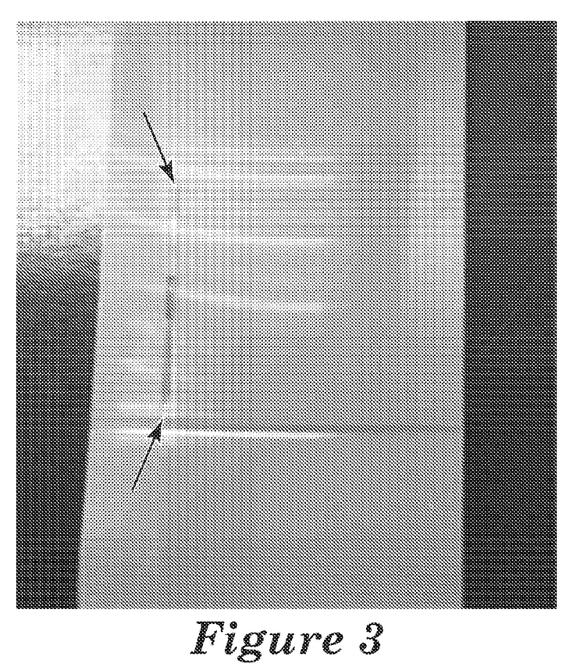
FIG. 3 shows liquid diffusion test results of an Example of the present invention.
Figure 4:
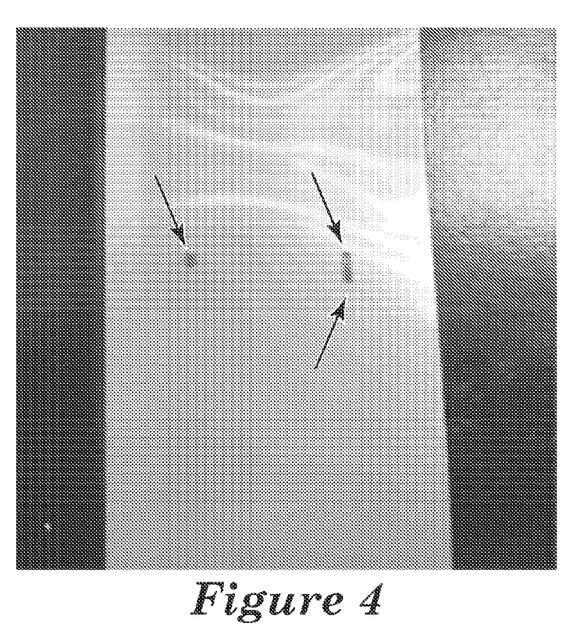
FIG. 4 shows liquid diffusion test results of a Comparative Example and an Example of the present invention on the left side and the right side, respectively.

An actual photo showing directional diffusion of an example is shown on the right side of FIG. 1 (B). The photo on the right side of FIG. 1 (B) shows the test result of Example 7. It can be seen from a comparison of this photo with FIG. 1 (A) (the left side of FIG. 1 (A) is the result of Comparative Example 1, and the right side of FIG. 1 (A) is the result of Comparative Example 2) and the left side of FIG. 1 (B) (Comparative Example 3) that Example 7 allows the test solution to make a more directional diffusion, compared with Comparative Examples 1 to 3. From the left to the right, FIGS. 2 (A)-(C) show the test results of Comparative Example 3, Example 3 and Example 1, respectively. FIG. 3 shows the test result of Example 4. The left side and the right side of FIG. 4 show the test results of Comparative Example 3 and Example 2, respectively. It can be seen from FIG. 2 to FIG. 4 that these examples also allow the liquid to diffuse in a directional manner Other Examples have the same results compared with Comparative 1 to 3. Arrows in the Figures are used to indicate the location of the dye path. When two arrows are used in the same photo, they indicate the locations of two ends of each dye path, respectively.

Figure 5:
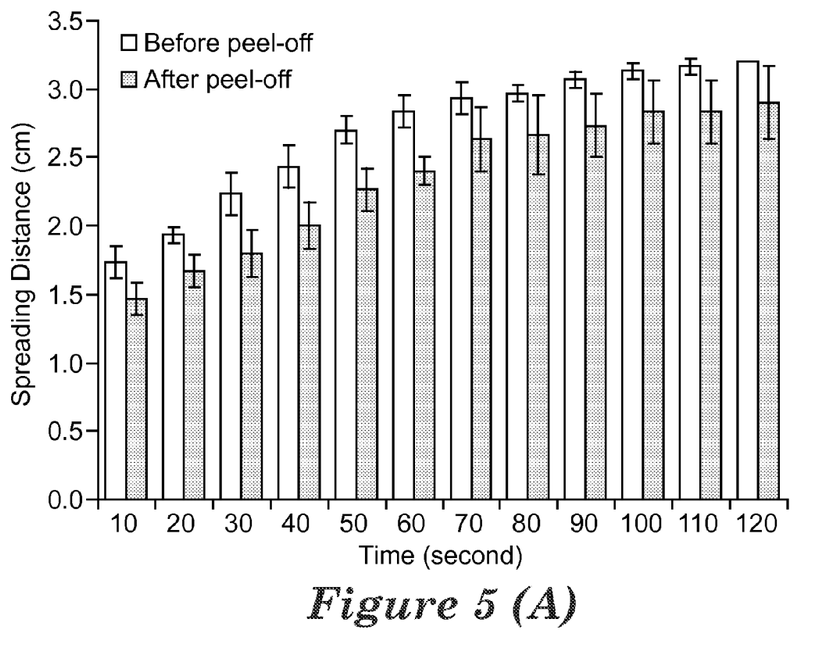

White columns in FIG. 5 (A) to FIG. 5 (G) successively correspond to the results of the diffusion distance tests of Examples 5 to 8 and Examples 10 to 12, respectively, in which FIG. 5 (A) corresponds to Examples 5, FIG. 5 (B) corresponds to Examples 6, FIG. 5 (C) corresponds to Examples 7, FIG. 5 (D) corresponds to Examples 8, FIG. 5 (E) corresponds to Examples 10, FIG. 5 (F) corresponds to Examples 11, and FIG. 5 (G) corresponds to Examples 12. It can be seen from FIG. 5 (A) to FIG. 5 (G) that coating an aqueous silicon dioxide solution on the BEF substrate having a texture of parallel sunken and raised patterns according to the present invention allows the liquid to diffuse in a unidirectional manner for about 1-2 cm within 10 sec, while the liquid is only able to diffuse for 0.5-0.7 cm in 10 min on a PET substrate without the texture of sunken and raised patterns. The silicon dioxide coating solution obtained in Example 9 will coagulate after being left to stand for one week. However, it is unlikely to affect the unidirectional diffusion of liquid if it is coated on the substrate before the silicon dioxide coating solution coagulates. As to Examples 13 to 17, the silicon dioxide coating solutions obtained in these examples do not have as good adhesion strength as those obtained in other example groups, but they can still cause liquid to diffuse in a single direction when dried. Therefore, it should be understood that the hydrophilic film coated with the aqueous silicon dioxide solution can be used on test strips for testing fluids, for example, test strips for testing body fluids, such as blood test strips, urine test strips, and the like. When the hydrophilic film coated with the silicon dioxide solution is used on these fluid test strips, they can lead the tested fluid to flow rapidly towards a test reaction zone to facilitate the reaction. Of course, the hydrophilic film of the present invention is not limited to the use of testing body fluids. Any test strips used for testing or guiding fluids can take advantages of the present invention.

2. Measurement of Surface Morphology

Figure 6:
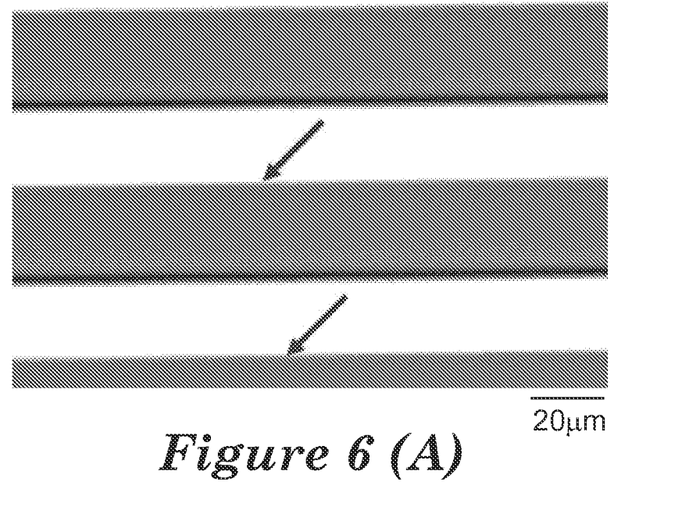
FIG. 6 shows SEM photos of a BEF film (A) that has not been modified by hydrophilic treatment and a BEF film (B) having a coat of silicon dioxide nanoparticles according to an Example of the present invention.

A scanning electron microscopy (SEM) (JOEL JSM5610-LV) is used for observing images of the film surface. FIG. 6 shows SEM photos of a BEF film (A) that has not been modified by hydrophilic treatment and a BEF film (B) that has a coat of silicon dioxide nanoparticles prepared according to Example 7. In the photos, arrows are used to indicate peaks of the micro-replicated prism structure. It can be seen clearly from FIG. 6 (B) that the substrate coated with the hydrophilic film has a lot of tiny silicon dioxide nanoparticles, and since the nanoparticles are substantially far smaller than the dimensions of the texture of sunken and raised patterns on the substrate, the texture of sunken and raised patterns of the substrate will not be filled up by the tiny silicon dioxide nanoparticles, but will keep the original texture and guide the moving direction of the fluid thereby.

3. Binding Strength Test

Binding strength test is conducted to check firmness of the hydrophilic coat. A protective tape is laminated with the BEF film coated with silicon dioxide nanoparticles prepared according to the Examples, and the tape is peeled off after the laminate is left at room temperature for 24 hrs. After the tape is peeled off, retained hydrophilicity is determined by the diffusion distance test. In the present invention, 3M 1T01L is used as a standard protective tape.

Results of the binding strength test for Examples 5 to 8 and Examples 10 to 12 are successively shown in FIG. 5 (A) to FIG. 5 (G), in which diffusion distances on the test film before lamination with the protective tape and after the protective tape is peeled off are represented by white columns and grey columns respectively. The value is the average of three test results.

The test results indicate that the hydrophilic films according to the examples of the present invention retain good hydrophilicity for guiding liquid to diffuse in a certain direction before laminating with and after peeling off the protective tape. Compared to a flat surface film, the BEF film has a texture of sunken and raised patterns, which can protect the aqueous silicon dioxide dispersion coated in the sunken areas and also have beneficial effect on firmness of the coat, and can prevent the aqueous silicon dioxide solution coated in the sunken areas from being peeled off when the protective tape is peeled off, thus retaining good hydrophilicity for the hydrophilic film.

4. Test with Resin Added

In order to improve the wetting performance of the aqueous silicon dioxide solution of the present invention on the substrate during coating process, a resin can optionally be added to the solution.

Table 3 shows the results indicating if a flocculent precipitate is generated after 2-20% TEGO VariPlus DS 50 resin is added to Example 5 and Example 11, and 2-20%% NeoCryl A-1127 resin is added to Example 11, and the solutions are left to stand. It is indicated as "No" in the table if no flocculent precipitate is generated.

TABLE 3 test results with added resin

| Standing time | 2% | 4% | 6% | 10% | 20% |
|---|---|---|---|---|---|
| Example 5 + TEGO VariPlus DS 50 resin with various concentrations | | | | | |
| 0 hr | No | No | No | No | No |
| 24 hrs | No | No | No | No | No |
| 48 hrs | No | No | No | No | No |
| Example 11 + TEGO VariPlus DS 50 resin with various concentrations | | | | | |
| 0 hr | No | No | No | No | No |
| 24 hrs | No | No | No | No | No |
| 48 hrs | No | No | No | No | No |
| Example 11 + NeoCryl A-1127 resin with various concentrations | | | | | |
| 0 hr | No | No | No | No | No |
| 24 hrs | No | No | No | No | No |
| 48 hrs | No | No | No | No | No |

It can be seen from the results in Table 3 that the addition of 2-20% resin, e.g., polyurethane resin, to the aqueous silicon dioxide solution will not cause flocculent precipitate; therefore the addition will not affect diffusion effect of the hydrophilic film, but will help improve wetting performance of the silicon dioxide coating solution on the substrate during coating process. Therefore, we can see that a resin can be added particularly to Examples 13-17 as an adhesive agent to help improve adhesion of the silicon dioxide coating solution to the substrate.

5. Test of pH Influence on the Aqueous Dispersion of Silicon Dioxide Nanoparticles A 3% aqueous dispersion of silicon dioxide nanoparticles is prepared from ST-XS silicon dioxide nanoparticles and deionized water. The dispersion has a pH value of 9.27, which is subsequently adjusted with a 45% aqueous NaOH solution to evaluate pH influence on the aqueous dispersion of silicon dioxide nanoparticles. The results are shown in Table 4.

TABLE 4 pH influence on the aqueous dispersion of silicon dioxide nanoparticles

| pH value | State of the aqueous dispersion of silicon dioxide nanoparticles |
|---|---|
| 9.27 | Clear |
| 10.04 | Clear |
| 11.40 | Clear |
| 12.31 | Clear |

Figure 7:
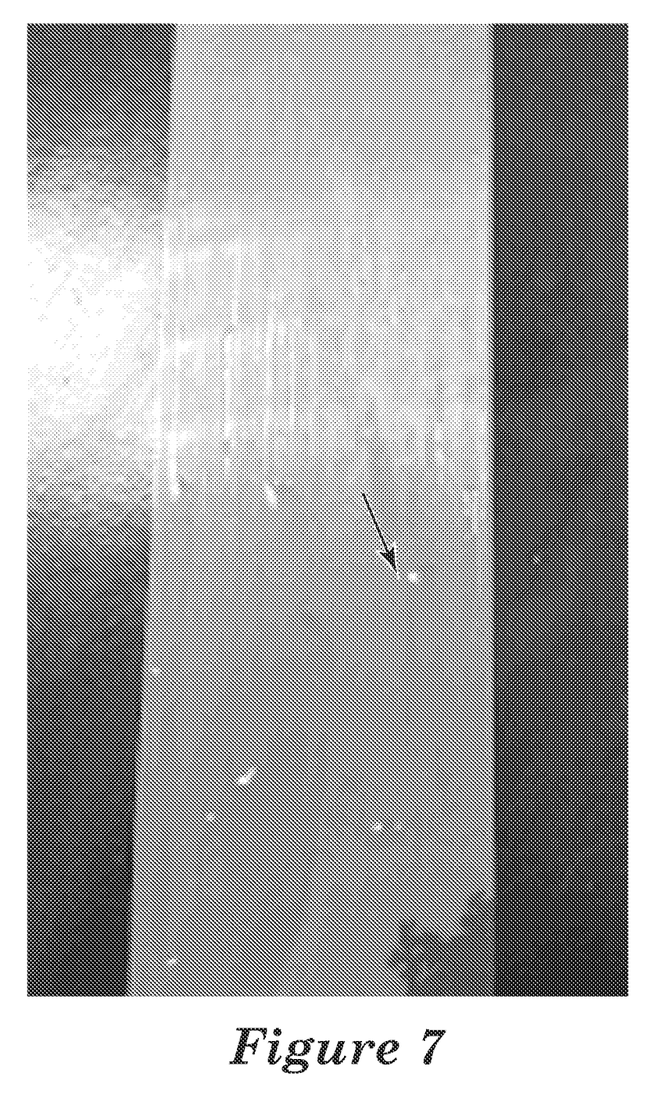
FIG. 7 shows liquid diffusion test result of an Example of the present invention.

FIG. 7 shows the test results of liquid diffusion on the coat of silicon dioxide particles obtained by coating the aqueous dispersion of silicon dioxide nanoparticles when pH value is 12.31. It can be seen from Table 4 and FIG. 7 that the coat of silicon dioxide particles obtained by coating and drying the aqueous dispersion of silicon dioxide nanoparticles on the substrate can still provide some effects to cause liquid to diffuse in a single direction even when the pH value of the aqueous dispersion of silicon dioxide nanoparticles is increased to 12.31. Therefore, pH value virtually has no significant influence on the aqueous dispersion of silicon dioxide nanoparticles. However, it should be understood that acidification can increase the amount of hydroxyl groups (—OH) in the silicon dioxide coating solution, thus enhancing hydrophilic effect; therefore, in order to obtain better effects of unidirectional liquid diffusion, pH value of the aqueous dispersion of silicon dioxide nanoparticles is preferably slightly acidic (as indicated by afore-mentioned Examples 1 to 17).

What is claimed is:

1. A hydrophilic film, comprising:
a substrate having a texture of parallel sunken and raised patterns, and
a hydrophilic coat, wherein the hydrophilic coat comprises a coat of silicon dioxide particles; and
wherein the substrate has a double-layer structure comprising a polyethylene terephthalate base substrate material coated with a polyacrylic acid substrate material.

2. The hydrophilic film according to claim 1, wherein the coat of silicon dioxide particles have an average size of 1 to 60 nm.

3. The hydrophilic film according to claim 1, wherein the coat of silicon dioxide particles is a dried layer of an aqueous dispersion of silicon dioxide particles, and the concentration of the aqueous dispersion of silicon dioxide particles is from 0.05% to 15% by weight.

4. The hydrophilic film according to claim 3, wherein the silicon dioxide particles in the aqueous dispersion of silicon dioxide particles are selected from the group consisting of the first group of silicon dioxide particles, a second group of silicon dioxide particles, a third group of silicon dioxide particles, and a combination thereof; and wherein the average size of the first group of silicon dioxide particles is no larger than 6 nm, the average size of the second group of silicon dioxide particles is larger than the first group of silicon dioxide particles but no larger than 25 nm, and the average size of the third group of silicon dioxide particles is larger than the second group of silicon dioxide particles but no larger than 60 nm.

5. The hydrophilic film according to claim 4, wherein the silicon dioxide particles in the coat of silicon dioxide particles are selected from the group consisting of the first group of silicon dioxide particles, the second group of silicon dioxide particles, the third group of silicon dioxide particles, and a combination thereof; when the concentration of the aqueous dispersion of silicon dioxide particles is no more than 0.5% by weight.

6. The hydrophilic film according to claim 4, wherein the silicon dioxide particles in the coat of silicon dioxide particles are selected from the group consisting of the first group of silicon dioxide particles, the second group of silicon dioxide particles, and a combination thereof; and wherein the concentration of the aqueous dispersion of silicon dioxide particles is from 0.5% to 10% by weight.

7. The hydrophilic film according to claim 4, wherein the silicon dioxide particles in the coat of silicon dioxide particles are selected from the first group of silicon dioxide particles; and wherein the concentration of the aqueous dispersion of silicon dioxide particles is from 10% to 15% by weight.

8. The hydrophilic film according to claim 1, wherein the depth of the texture of parallel sunken and raised patterns is half of the interval between adjacent two highest points or lowest points.

9. A hydrophilic film according to claim 1, wherein the polyacrylic acid substrate material comprises a surface having a texture of regular parallel sunken and raised patterns, wherein the patterns have a repeating prism structure.

10. A method for preparing the hydrophilic film according to claim 1, the method comprising:
preparing an aqueous dispersion of silicon dioxide particles, wherein the average size of the silicon dioxide particles is 1 to 60 nm, and the concentration of the silicon dioxide particles is 0.05% to 15% by weight;
coating the aqueous dispersion of silicon dioxide particles on the substrate, wherein the substrate has a texture of parallel sunken and raised patterns; and
drying the substrate coated with the aqueous dispersion of silicon dioxide particles.

11. The method according to claim 10, further comprising adjusting the pH value of the aqueous dispersion of silicon dioxide particles to 2-5 with an acid.

12. The method according to claim 10, wherein the aqueous dispersion of silicon dioxide particles further comprises a resin.

13. The method according to claim 12, wherein concentration of the resin is 0.1-20% by weight.

14. The method according to claim 10, wherein the aqueous dispersion of silicon dioxide particles further comprises a surfactant.

15. A method of monitoring the level of a substance in the blood or urine, comprising contacting blood or urine with the hydrophilic film according to claim 1.

16. A strip comprising the hydrophilic film according to claim 1.

17. A strip according to claim 16, wherein upon contact with a hydrophilic liquid, the hydrophilic liquid diffuses rapidly in one direction.

18. A method of monitoring the level of a substance in the blood or urine, comprising contacting blood or urine with the strip according to claim 16.

19. A method according to claim 18, wherein the substance is glucose.

* * * * *

UNITED STATES PATENT AND TRADEMARK OFFICE
CERTIFICATE OF CORRECTION

PATENT NO. : 9,696,318 B2  
APPLICATION NO. : 14/430145  
DATED : July 4, 2017  
INVENTOR(S) : David Chen Page 1 of 1

It is certified that error appears in the above-identified patent and that said Letters Patent is hereby corrected as shown below:

Column 8  
Line 35, Delete "manner" and insert -- manner. --, therefor.

Column 11  
Line 10, In Claim 1, after "of" insert -- acidified --.

Column 11  
Line 26, In Claim 4, delete "the" and insert -- a --, therefor.

Column 11  
Line 41 (Approx.), In Claim 5, delete "when" and insert -- and wherein --, therefor.

Signed and Sealed this  
Twenty-first Day of November, 2017

Joseph Matal  
*Performing the Functions and Duties of the*  
*Under Secretary of Commerce for Intellectual Property and*  
*Director of the United States Patent and Trademark Office*